US010350231B2

(12) United States Patent
Roach et al.

(10) Patent No.: US 10,350,231 B2
(45) Date of Patent: Jul. 16, 2019

(54) USE OF CLADRIBINE FOR TREATING AUTOIMMUNE INFLAMMATORY DISEASE

(71) Applicant: Chord Therapeutics S.a.r.l., Plan-les-Ouates (CH)

(72) Inventors: Arthur Henry Roach, Geneva (CH); Konrad Rejdak, Lublin (PL)

(73) Assignee: Chord Therapeutics S.a.r.l., Plan-les-Ouates (CH)

( * ) Notice: Subject to any disclaimer, the term of this patent is extended or adjusted under 35 U.S.C. 154(b) by 71 days.

(21) Appl. No.: 15/114,758

(22) PCT Filed: Jan. 27, 2015

(86) PCT No.: PCT/GB2015/050177
§ 371 (c)(1),
(2) Date: Jul. 27, 2016

(87) PCT Pub. No.: WO2015/114315
PCT Pub. Date: Aug. 6, 2015

(65) Prior Publication Data
US 2016/0339049 A1 Nov. 24, 2016

(30) Foreign Application Priority Data

Jan. 29, 2014 (GB) .................................. 1401465.8

(51) Int. Cl.
| A61K 31/7076 | (2006.01) |
| A61K 47/02 | (2006.01) |
| A61K 9/00 | (2006.01) |
| A61K 9/08 | (2006.01) |
| A61K 9/48 | (2006.01) |

(52) U.S. Cl.
CPC ........ *A61K 31/7076* (2013.01); *A61K 9/0019* (2013.01); *A61K 9/08* (2013.01); *A61K 9/485* (2013.01); *A61K 9/4825* (2013.01); *A61K 9/4858* (2013.01); *A61K 9/4866* (2013.01); *A61K 47/02* (2013.01)

(58) Field of Classification Search
CPC .. A61K 31/7076; A61K 47/02; A61K 9/4866; A61K 9/4858; A61K 9/4825; A61K 9/08; A61K 9/0019; A61K 9/485
See application file for complete search history.

(56) References Cited

U.S. PATENT DOCUMENTS

| 5,208,327 | A |   | 5/1993 | Chen |   |
| 5,310,732 | A | * | 5/1994 | Carson | .................. C07H 19/16 514/46 |
| 5,506,214 | A | * | 4/1996 | Beutler | .................. A61K 31/70 514/45 |
| 9,891,219 | B2 | * | 2/2018 | Lennon | ................ A61K 31/439 |
| 2010/0092478 | A1 |   | 4/2010 | Lennon et al. |   |
| 2010/0239580 | A1 |   | 9/2010 | Del Rio et al. |   |
| 2013/0039905 | A1 | * | 2/2013 | Pugliese | .............. A61K 31/549 424/133.1 |

FOREIGN PATENT DOCUMENTS

| EP | 0173059 A2 | 3/1986 |   |
| EP | 0 626 853 B1 | * 4/2000 | ............. A61K 31/70 |
| EP | 2263678 A2 | 12/2010 |   |
| WO | WO-2004/087100 A2 | 10/2004 |   |
| WO | WO-2004087100 A2 | 10/2004 |   |
| WO | WO-2006067141 A1 | 6/2006 |   |
| WO | WO-2008097596 A2 | 8/2008 |   |
| WO | WO-2011/032204 A1 | 3/2011 |   |
| WO | WO-2011080344 A1 | 7/2011 |   |

OTHER PUBLICATIONS

Porter et al., The Merck Manual of Diagnosis and Therapy, 19th Ed., Neuromyelitis Optica, Chapter 184, only p. 1783 supplied.*
Porter et al., The Merck Manual of Diagnosis and Therapy, 19th Ed., Neuromyelitis Optica, Chapter 184, only p. 1783 supplied, 2011.*
PCT/GB2015/050177, International Preliminary Report on Patentability dated Aug. 11, 2016, 6 pgs.
PCT/GB2015/050177, International Search Report dated Mar. 9, 2015, 4 pgs.
United Kingdom Application No. GB1304194.2, Search Report dated Jul. 16, 2013, 1 pg.
Awad, A., et al., "Idiopathic Transverse Myelitis and Neuromyelitis Optica: Clinical Profiles, Pathophysiology and Therapeutic Choices", Current Neuropharmacology, 9, (2011), 417-428.
Ghosh, A., et al., "Cladribine in the treatment of IgM paraproteinemic polyneuropathy", Neurology, 59, (2002), 1290-1291.
Holmøy, T., et al., "The immunological basis for treatment of multiple sclerosis.", Scand. J. Immunol., 66, (2007), 374-382.
Kazimierczuk, Z., et al., "Synthesis of 2'-deoxytubercidin, 2'-deoxyadenosine, and related 2'-deoxynucleosides via a novel direct stereospecific sodium salt glycosylation procedure", J. Am. Chem. Soc., 106, (1984), 6379-6382.
Laugel, B., et al., "Cladribine inhibits cytokine secretions by T cells independently of deoxycytidine kinase activity", Journal of Neuroimmunology, 240-241, (2011), 52-57.
Leist, T.P., et al., "Cladibine: Mode of Action and Implications for Treatment of Multiple Sclerosis", Clinical Neuropharmacology, 34, (Jan.-Feb. 2011), 28-35.
Ohta, A., "Role of G-protein-coupled adenosine receptors in downregulation of inflammation and protection from tissue damage", Nature, 414(6866), (2001), 916-920.
Ontaneda, D., et al., "Multiple Sclerosis: New Insights in Pathogenesis and Novel Therapeutics", Annu. Rev. Med., 63, (2012), 389-404.
Sa, M.J., et al., "Etiopathogenesis, Classical Immunotherapy and Innovative Nanotherapeutics for Inflammatory Neurological Disorders", Current Nanoscience, 7, (2011), 2-20.

(Continued)

*Primary Examiner* — Lawrence E Crane
(74) *Attorney, Agent, or Firm* — Schwegman Lundberg & Woessner, P.A.

(57) ABSTRACT

2-Chloro-2'-deoxyadenosine, hereinafter referred to as cladribine, or a pharmaceutically acceptable salt thereof may be used in the treatment or amelioration of neuromyelitis optica, hereinafter referred to as NMO e.g. in patients known to have NMO-IgG seropositivity or in patients optic neuritis, myelitis and at least two of MRI evidence of contiguous spinal cord lesion 3 or more segments in length, onset brain MRI nondiagnostic for multiple sclerosis or NMO-IgG seropositivity.

9 Claims, 1 Drawing Sheet

(56) References Cited

OTHER PUBLICATIONS

"Neuromyelitis Optica, IgG Autoantibodies: Test Details", LabCorp, 2018 [online]. Retrieved on Dec. 16, 2018. Retrieved from Internet: <htttps://www.labcorp.com/test-menu/31901/neuromyelitis-optica-igg-autoantibodies >, 4 pgs.
Jarius, S., et al., "Mechanisms of Disease: aquaprin-4 antibodies in neuromyelitis optica", Nature Clinical Practice: Neurology, (Mar. 11, 2008), 13 pgs.
Lennon, V.A., et al., "A serum autoantibody marker of neuromyelitis optica: distinction from multiple sclerosis", Lancet, 264, (2004), 2106-2112.
Shimizu, Y., et al., "Development of extensive brain lesions following interferon beta therapy in relapsing neuromyelitis optica and longitudinally extensive myelitis", J. Neurol., 255, (2008), 305-307.
Uzawa, A., et al., "Different responses to interferon beta-1b treatment in patients with neuromyelitis optica and multiple sclerosis", European Journal of Neurology, 17, (2010), 672-676.
Van Herle, K., et al., "Integrative Continuum: Accelerating Therapeutic Advances in Rare Autoimmune Diseases", Annu. Rev. Pharmacol. Toxicol., 52, (2012), 523-547.
Wingerchuk, D.M., et al., "Revised diagnostic criteria for neuromyelitis optica", Neurology 66, (2006), 1485-1489.
European Application Serial No. 15702549.5, Notice of Opposition filed Jul. 18, 2018, 49 pgs.
Bellanger, "Multiple Sclerosis Treatment Update", US Pharmacist, vol. 37, No. 1, (2012), 42-45.
Chong, et al., "A Review of Multiple Sclerosis with Asian Perspective", Med J Malaysia, vol. 63, No. 5, (2008), 356-361.
Giovannoni, et al., "A Placebo-Controlled Trial of Oral Cladribine for Relapsing Multiple Sclerosis", N. Engl. J. Med., vol. 362, (2010), 416-426.
Grossmann, et al., "Multiple sclerosis pharmacogenetics: personalized approach towards tailored therapeutics", EPMA Journal, vol. 1, (2010), 317-327.
Gurcan, et al., "A Review of the Current Use of Rituximab in Autoimmune Diseases", International Immunopharmacology, vol. 9, (2009), 10-25.
Hartung, et al., "Development of oral cladribine for the treatment of multiple sclerosis", J Neural., vol. 257, (2010), 163-170.
Jurynczyk, et al., "Expert opinions on the diagnosis and treatment of patients with AQP4-negative NMO/MS overlapping syndromes", J Neural Neurosurg Psychiatry, vol. 86, (2015), e4.
Jurynczyk, et al., "Status of diagnostic approaches to AQP4-IgG seronegative NMO and NMO/MS overlap syndromes", J. Neural., vol. 263, No. 1, (2016), 140-149.
Kim, et al., "Quantitative Measurement of Anti-Aquaporin-4 Antibodies by Enzyme-Linked Immunosorbent Assay using Purified Recombinant Human Aquaporin-4", Multiple Sclerosis Journal, vol. 18, No. 5, (May 2012), 578-586.
Kimbrough, et al., "Treatment of neuromyelitis optica: Review and Recommendations", Multiple Sclerosis and Related Disorders, vol. 1, (2012), 180-187.
Mitosek-Szewczak, et al., "Impact of Cladribine Therapy on Changes in Circulating Dendritic Cell Subsets, T Cells and B Cells in Patients with Multiple Sclerosis", Journal of the Neurological Sciences, vol. 332, (2013), 35-40.
Rejdak, et al., "Multiple sclerosis: a practical overview for clinicians", British Medical Bulletin, vol. 95, (2010), 79-104.
Rodrigues De Almeida, Camila, "Frequencia do anticorpo IGG NMO em pacientes com neuromielite optica no rio de janeiro e sua influencia no prognostico da enfermidade", PhD thesis, (2015).
Rosenzweig, "Disease-modifying therapy in adult relapsing remitting multiple sclerosis", Formulary, vol. 45, (2010), 252-262.
Trebst, et al., "Update on the diagnosis and treatment of neuromyelitis optica: Recommendations of the Neuromyelitis Optica Study Group (NEMOS)", J. Neural., vol. 261, (2014), 1-16.
Wingerchuk, et al., "The Spectrum of Neuromyelitis Optica", Lancet Neural., vol. 6, (2007), 805-815.
European Application No. 15702549.5, Response to Opposition filed Nov. 7, 2018, 14 pgs.
European Patent Application No. 15702549.5, Summons to Attend Oral Proceedings and Provisional Opinion of the Opposition Division mailed Feb. 26, 2019, 16 pgs.

\* cited by examiner

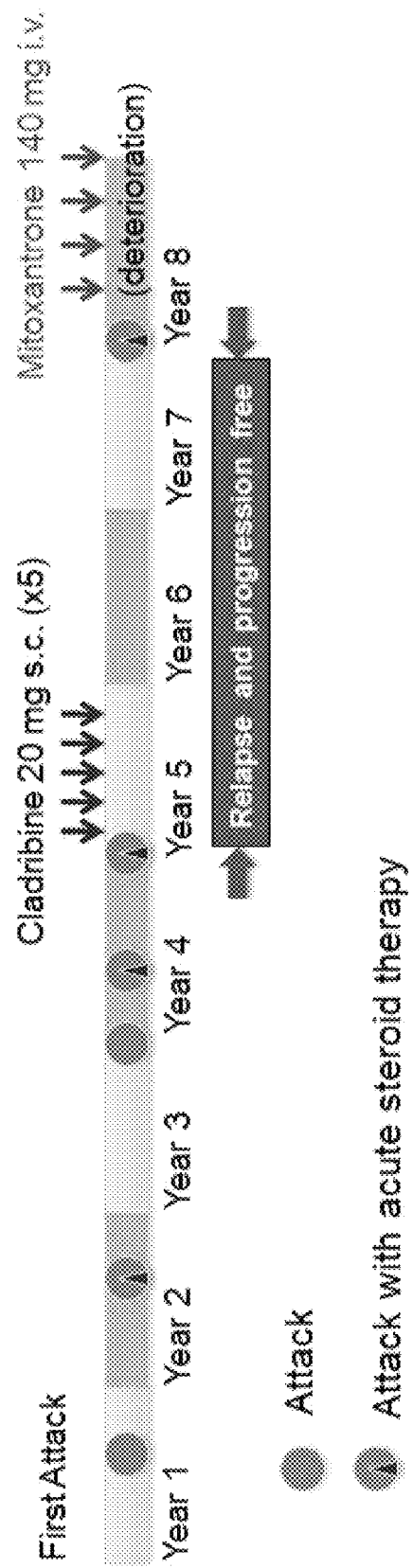

USE OF CLADRIBINE FOR TREATING AUTOIMMUNE INFLAMMATORY DISEASE

RELATED APPLICATIONS

This application is a U.S. National Stage Filing under 35 U.S.C. 371 from International Application No. PCT/GB2015/050177, filed on Jan. 27, 2015, and published as WO 2015/114315 A1 on Aug. 6, 2015, and which claims the benefit of priority under 35 U.S.C. § 119 to United Kingdom Patent Application No. 1401465.8, filed on Jan. 29, 2014, each of which is hereby incorporated by reference herein in its entirety.

FIELD OF THE INVENTION

The present invention relates to the use of 2-chloro-2'-deoxyadenosine, hereinafter referred to as cladribine, or a pharmaceutically acceptable salt thereof, for treating or ameliorating an autoimmune, inflammatory disorder, in particular the autoimmune inflammatory disorder neuromyelitis optica, hereinafter referred to as NMO, also known as Devic's disease or Devic's syndrome.

BACKGROUND TO THE INVENTION

Inflammatory diseases are a large family of disorders in which the activity of elements of the immune system cause a wide range of signs and symptoms in the body including fever, rash, pain, swelling, weakness and many types of tissue damage. A subset of inflammatory diseases are also classified as autoimmune diseases because of evidence that in these cases the activation of the immune system is linked to an aberrant reactivity against some of the body's own normal proteins or other structures. Autoimmune inflammatory diseases can result in symptoms that range from moderate to severe such as blindness, being wheelchair bound or bedridden, or even to death. Variability in disease presentation is common and severity can vary markedly between patients with the same disorder.

NMO is a rare autoimmune inflammatory disorder with prevalence estimated as 1.5-4.4 per 100,000 of the population resulting in a calculated 12,000-35,000 patients in the US and Europe combined. The age of onset can vary from adolescence or even childhood, to late adulthood with a median of late 30's. There is a marked female to male preponderance reported to be as high as 9:1.

Clinical onset of NMO is usually acute and in two thirds of cases a prodrome of flu-like symptoms may precede neurological problems. Typically symptoms appear strongly in attacks (relapses) lasting several weeks, separated by periods of remission lasting several months. Nonetheless, as the disease progresses symptoms become increasingly present during the remission periods. The main symptoms of NMO are loss of vision and spinal cord function. Optic neuritis may manifest itself as visual impairment with decreased visual acuity, possibly with loss of colour vision. More than half of patients with relapsing NMO become blind in one or both eyes in five years. The effect on spinal cord function usually leads to muscle weakness, reduced sensation and even to loss of bladder and bowel control. A typical NMO sufferer may have acute and severe spastic weakness of the legs or even all four limbs with sensory signs and often accompanied by loss of bladder control. Death can result in some cases due to disruption of breathing during an attack. Pathology studies have revealed lesions in the optic nerve and spinal cord with evidence of inflammation and demyelination.

NMO, whilst displaying some symptoms which are similar to multiple sclerosis, (MS), such as recurrent attacks of neurological symptoms associated with disease activity in the optic nerve and spinal cord and leading to various disabilities with variable recovery, is in fact clearly distinct from MS clinically, radiologically, pathologically, and in terms of treatment approaches. This distinction is of great importance as management of NMO and prognosis of the disease are fundamentally different from MS.

In regard to clinical symptoms, the course of disease in the majority of both NMO and MS patients includes attacks (relapses) that typically last for weeks during which old symptoms may exacerbate and new ones appear. In comparison with MS the relapses in NMO are generally more frequent and more severe. In NMO these attacks alternate with stable periods during which the disabilities that appeared in the last relapse are maintained to some extent. In contrast, in early MS the symptoms that appeared during the preceding relapse(s) may resolve completely. In patients with later MS (and in a subset of cases called progressive MS) there is a slowly increasing severity of symptoms between relapses, and even a cessation of distinguishable relapse activity. This pattern is rare in NMO.

In regard to radiological findings, magnetic resonance imaging has shown that the spinal cord lesions in NMO patients, are longitudinally extensive involving three or more segments and are usually symmetrical (involving both sides of the cord to similar extents), whereas in MS the lesions in spinal cord are not as long and generally on one side of the cord only or predominantly. Lesions are infrequent in the brain at diagnosis and are generally not an important contributor to disability in NMO, whereas brain lesions are common and sometimes symptomatic in MS. Optic nerve lesions occur in both diseases.

In regard to involvement of elements of the immune system, in MS the attacks are believed to be mediated by infiltration of the immune system's T lymphocyte cells into the central nervous system along with activation of local microglial cells. Autoantibody involvement is suspected and the pertinent autoantigens are believed to be primarily myelin components. In NMO the disease is believed to be caused in part by serum autoantibodies called NMO-IgG. These antibodies target the protein aquaporin 4 (AQP-4) in the cell membrane of astrocytes. Aquaporin 4 acts as a channel for the transport of water across the cell membrane. It is found in the processes of the astrocytes that surround the blood-brain barrier, a system responsible for preventing substances in the blood from crossing into the brain. In NMO the blood-brain barrier is weakened, but at present it is not known how the NMO-IgG immune response results in demyelination. It is known, however, that the distribution of lesions in the NMO brain correlates with AQP-4 expression. T cell and B cell involvement is implied by the belief that azathioprine and rituximab are effective therapies, but eosinophils are the predominant cell type found in lesions upon pathological examination, in contrast to the predominant T cell pathology seen in MS.

Wingerchuk, D. M. et al in 2006 in *Neurology*, Vol. 66 no. 10 pp 1485-1489 proposed revised diagnostic criteria for defining NMO which required optic neuritis, myelitis and at least two of three supportive criteria, namely MRI evidence of continuous spinal cord lesion three or more segments in length, onset brain MRI nondiagnostic for multiple sclerosis or NMO-IgG seropositivity. CNS involvement beyond the optic nerves and spinal cord is compatible with NMO.

There is currently no cure for NMO nor is there an FDA-approved or EMA-approved treatment for the disease due to the lack of adequate double-blind randomized placebo-controlled trials. However, symptoms can be treated. Attacks in NMO may be treated with short courses of intravenous corticosteroids such as methylprednisolone W. No controlled trials have established the effectiveness of treatments for the prevention of attacks.

Many clinicians consider that long-term immunosuppression is required to reduce the frequency and severity of attacks. The most commonly used immunosuppressive treatments are azathioprine plus prednisone, mycophenolate mofetil plus prednisone, rituximab, mitoxantrone, intravenous immunoglobulin and cyclophosphamide, with rituximab being considered the most promising treatment for relapsing NMO. Rituximab is a monoclonal antibody that targets clusters of differentiation (CD) 20 expressing cells, but its exact mode of action remains unclear. Furthermore, treatment with rituximab is known to cause side effects such as progressive multifocal leukoencephalopathy. Eculizumab is a recently tested experimental treatment in NMO.

There are a large number of potential therapies available for testing in autoimmune inflammatory diseases. However, it has not proven possible to predict which treatments, addressing which steps in the known pathology, will be successful in a given disease, for example in NMO. This is amply illustrated with two of the most widely used therapeutic strategies for disease course modification in relapsing MS. They are glatiramer acetate and one of the several marketed forms of the cytokine interferon beta. Both these treatments reduce relapse rate and lesion activity in the brain and spinal cord of MS patients. However, when interferon beta was tested in NMO, considered until then to be a disease similar to MS, it was unexpectedly and surprisingly found to have the opposite of the expected effect and to exacerbate NMO. Development of extensive brain lesions (Shimizu Y. et al., *J. Neurol.*, 255; 305-307; (2008)) and clinical worsening (Uzawa A. et al., *Eur. J. Neurol.*, 17; 672-676; (2010)) were reported in NMO patients treated with IFN-beta. Glatiramer acetate is believed to work by producing a beneficial change in T cell phenotype from the proinflammatory Th1 type to the regulatory Th2 type. Once again this well-proven treatment for MS has not been found to be effective and is not recommended for NMO (Awad A. and Stuve O., *Current Neuropharmacology;* 9; 417-428 (2011)).

Cladribine or 2-chloro-2'-deoxyadenosine has been used successfully in the oncology field with marked effects on lymphocytes. It has been found to be an effective treatment of hairy cell leukemia, chronic lymphocytic leukemia and some T cell malignancies. The addition of a chlorine atom at the 2 position of the adenine rings renders the molecule resistant to deamination by adenosine deaminase. Once taken up by cells in the body cladribine is converted enzymatically to cladribine triphosphate. Once formed inside the cell the unnatural chlorine-carrying cladribine derived nucleotides do not easily leave the cell and they can interact with cellular enzymes that normally work on the cell's natural deoxynucleotides. Two critical enzymes influencing the levels of cladribine nucleotides within a cell are cytidine kinase (CK) and nucleotidase (NT). It has been shown that levels of CK and NT enzyme expression vary between cell types and that lymphocytes have an especially high ratio of CK to NT expression. The combination of cladribine's resistance to adenosine deaminase and lymphocytes' high CK:NT ratio leads to the concentration and retention of cladribine nucleotides in human lymphocytes. This unique situation is responsible for cladribine's selectivity towards T and B lymphocytes when administered systemically.

The accumulation of cladribine nucleotides in lymphocytes has several known deleterious effects on the survival and function of lymphocyte cells. The result of these effects is death of both dividing and non-dividing lymphocytes. As a result it has been suggested that cladribine may be used for treating multiple sclerosis (see U.S. Pat. No. 5,506,214).

In addition to the foregoing effects of cladribine to cause death of lymphocytes by mechanisms dependent upon its intracellular phosphorylation, there are other means by which cladribine can affect immune system function. Induced cytokine production by human lymphocytes stimulated in culture by anti-CD3 and anti CD28 antibodies is decreased by cladribine treatment under conditions in which phosphorylation by CK is blocked and lymphocyte death does not occur (Laugel B. et al; *J. Neuroimmunol;* (2011); 240-241; 52-57).

Cladribine also binds with high affinity at a class of cell surface receptors called A2A (adenosine receptor class 2a). A2A receptors are found on T lymphocytes as well as other cell types in brain and the vasculature, and agents which bind A2A receptors have been shown to regulate overactive immune responses (Ohta A, Sitkovsky M. *Nature* 414: 916-20 (2001)).

Cladribine has also been reported to have been used to treat a single patient suffering from IgM associated inflammatory peripheral neuropathy that, unlike MS and NMO, is a non-relapsing, non-remitting disease. The drug was administered by intravenous infusion and levels of IgM antibodies were followed. (see Ghosh A. et al.; *Neurology;* 59; 1290-1291; (2002)). The patient had been on a deteriorating course for two years with increased symptoms and increased IgM levels, despite other treatments. After treatment with two courses of cladribine IgM levels declined slowly over a period of more than one year, at which time a symptomatic improvement was noted, and the improved symptoms and reduced IgM levels were both maintained for several years without further cladribine treatment.

Whilst cladribine has been used for treating other diseases including some leukemias and multiple sclerosis, and dosage regimens have been described (see EP 2263678) it could not have been predicted that cladribine would be effective in treating NMO. The inventors have unexpectedly found that cladribine may be beneficial in the treatment or amelioration of the autoimmune inflammatory disorder neuromyelitis optica. The inventors have further unexpectedly found that the sum of cladribine's effects on the immune system allows a short period of treatment (several weeks) to provide beneficial effects on the disease for a prolonged period of over 18 months without the need for retreatment at approximately yearly intervals.

SUMMARY OF THE INVENTION

According to one aspect of the invention there is provided 2-chloro-2'-deoxyadenosine, known as cladribine, or a pharmaceutically acceptable salt thereof, for use in the treatment or amelioration of neuromyelitis optica.

The cladribine may be for use in the treatment of a patient known to be NMO-IgG seropositive.

It may also be for use in the treatment of a patient known to have optic neuritis, myelitis and at least two of: MRI evidence of contiguous spinal cord lesion 3 or more segments in length, onset brain MRI nondiagnostic for multiple sclerosis or NMO-IgG seropositivity According to a second aspect of the invention there is provided a pharmaceutical composition comprising 2-chloro-2'-deoxyadenosine, known as cladribine, for use in the treatment or amelioration of neuromyelitis optica. The composition preferably comprises one or more pharmaceutically acceptable excipients.

The composition comprises from 1 milligram (mg) to 20 mg of cladribine per unit dose, preferably from 2.5 mg to 15 mg, most preferably from 8 mg to 12 mg per unit dose.

Preferably the composition is to be administered orally. For oral administration the composition may be presented as a tablet, a capsule or a liquid formulation. It may also be presented in a liquid formulation suitable for injection.

Preferably the composition consists of cladribine or a pharmaceutically acceptable salt thereof.

According to another aspect of the invention there is provided use of 2-chloro-2'-deoxyadenosine (cladribine), or a pharmaceutically acceptable salt thereof, in the preparation of a medicament for the treatment or amelioration of neuromyelitis optica.

Preferably the medicament is to be administered orally and is presented in the form of a tablet, capsule or liquid formulation.

An effective cumulative dose or amount of from 1 to 6 mg cladribine per kilogram of patient body weight (mg/kg) in the medicament is taken over a period of from one to two years. Preferably the effective cumulative amount comprises from 1.5 mg/kg to 3.5 mg/kg of cladribine.

According to yet another aspect of the invention there is provided a method of treating or ameliorating neuromyelitis optica in a subject suffering from the disease comprising administering to the subject, or patient, a pharmaceutical composition comprising an effective amount of 2-chloro-2'-deoxyadenosine (cladribine), or a pharmaceutically acceptable salt thereof.

The composition is presented in unit dose form such as a tablet, capsule or liquid formulation for oral administration.

The pharmaceutical composition may be administered daily as a single dose.

The effective amount may be determined empirically as the effective cumulative amount of cladribine administered on between 5 and 20 dosing days, distributed over between 1 and 16 weeks, preferably between 5 and 10 weeks, that results in a reduction of CD3+ T cells of between 30 and 80%, preferably between 40 and 60% relative to pre-treatment levels.

DETAILED DESCRIPTION OF THE INVENTION

Definitions

"Amelioration" of a disease refers to the ability of a pharmaceutical composition or treatment to make the patient undertaking the treatment better or to improve the symptoms of the disease suffered by the patient or to make the disease more tolerable.

As used herein, "treating" or "treatment" means reducing, hindering the development of, controlling, alleviating and/or reversing the symptoms in an individual to which cladribine has been administered, as compared to the symptoms of an individual not being treated.

"Effective amount" of a composition refers to a composition which contains cladribine in an amount sufficient to provide a therapeutic dose over the course of treatment.

The term "unit dose" refers to physically discrete units suitable as unitary dosages for administration to patients, each such unit containing a predetermined quantity of cladribine calculated to produce the desired therapeutic effect in association with pharmaceutically acceptable ingredients.

The terms "effective cumulative amount" and "effective cumulative dose" refer to the total amount of cladribine given to a patient over time, i.e. the total dose of cladribine given in a series of treatments.

FIG. 1 is a schematic representation of the progress of the disease in a woman diagnosed with NMO and treated with 100 mg of cladribine subcutaneously.

Cladribine and/or its pharmaceutically acceptable salts may be used in the practice of this invention. Suitable pharmaceutically acceptable salts refers to non-toxic acid addition salts that are generally prepared by reacting a compound with a suitable organic or inorganic acid. Examples of suitable salts include the hydrochloride, hydrobromide, sulphate, phosphate, citrate, acetate and maleate.

Cladribine may be prepared by processes well known in the art, such as those described in EP 173,059, U.S. Pat. No. 5,208,327 and Robins et al., *J. Am. Chem. Soc.*, 106; 6379; (1984).

Whilst cladribine may be administered intravenously or subcutaneously, oral delivery is preferred for several reasons, the most important of which is patient compliance. There is also generally a cost benefit, since the cost of parenteral administration is much higher due to the necessity for the administration to be carried out by a doctor or nurse in a clinic, hospital or other specialised facility.

Oral administration of cladribine may be in capsule, tablet, oral suspension or syrup form, with capsules or tablets being preferred. Oral formulations of cladribine have been described in WO 2004/087100.

Pharmaceutical compositions of cladribine for use in the present invention may further comprise one or more pharmaceutically acceptable excipients such as alum, stabilizers, antimicrobial agents, buffers, colouring agents, flavouring agents, flavouring agents, adjuvants and the like. Where the composition is in the form of a tablet or capsule for oral administration conventional excipients, such as binding agents, fillers, lubricants, glidants, disintegrants and wetting agents may be included.

Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulphate. Glidants include, but are not limited to silicon dioxide.

Tablets or pills may be provided with an enteric layer in the form of an envelope that serves to resist disintegration in the stomach and permits the active ingredients to pass intact into the duodenum or to be delayed in release. A variety of materials can be used for enteric layers or coatings, including polymeric acids or mixtures of such acids with such materials as shellac, shellac and cetyl alcohol, cellulose acetate phthalate and the like.

Compositions of this invention may also be liquid formulations including, but not limited to, aqueous or oily suspensions, solutions, emulsions, syrups, and elixers. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminium stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Treatments may be given as a number of courses, each course comprising for example five consecutive days of administration of one or two tablets or capsules containing 10 mg cladribine or drinking or infusing a similar amount of cladribine in a liquid formulation on each of five days. Patients suffering from NMO may, for example, receive two such courses of treatment separated by several days, for example from 21 to 30 days, at the beginning of the first treatment. This may be followed by two additional courses, also separated by from 21 to 30 days at the beginning of the second year of treatment, or only the first two courses may be used in a patient's therapy.

The total cumulative dose of cladribine over the one or two years of treatment may be from 1 to 6 mg/kg body weight, preferably from 1.5 to 4.0 mg/kg, most preferably 1.75 to 3.5 mg/kg per unit dose. Thus, for an 80 kg patient taking 3.5 mg/kg the total dose may be approximately 280 mg, consisting of 28 tablets containing 10 mg of cladribine each, distributed over 10 or 20 dosing days where on some days one tablet is taken whilst on others two tablets or three tablets are taken. When administered as a liquid formulation by injection the dose regimen may be halved.

Alternatively, the baseline level of cluster of differentiation (CD)3+ T lymphocytes in a patient's blood sample is measured before the patient is given one five day course of treatment with a cumulative cladribine dose of 0.5 to 3.5 mg/kg. Following a period of non-treatment of from 3 to 6 weeks the lymphocyte cell numbers are re-measured. Further doses then may be administered in order to obtain a 50%±10% reduction in the numbers of CD3+ T lymphocytes.

Cladribine has been found to have a unique combination of mechanisms of action that translates into a unique profile of functional effects on autoimmunity and inflammatory mechanisms. Whilst it has mechanisms that lead to direct killing of lymphocytes with sparing of other immune and non-immune cell types, it also has an effect on lymphocytes that is independent of cytotoxic mechanisms and can affect the function of dendritic cells. Cladribine has been found unexpectedly to induce cytokine and antibody production and a reduction in disease severity effects that long outlast its presence in the body and its effect on B lymphocyte cells.

The invention will be further described with reference to the following examples:—

Example 1

Powder in Capsule Formulation

| | |
|---|---|
| Cladribine | 10 mg |
| Microcrystalline cellulose | 100 mg |
| Lactose | 77.8 mg |
| Croscarmellose sodium | 10 mg |
| Silicon dioxide | 0.2 mg |
| Magnesium stearate | 2 mg |
| Hard gelatin size | 1 capsule shell |

Example 2

Injectible Formulation

| | |
|---|---|
| Cladribine in sterile aqueous solution of sodium chloride | 1 mg/ml 0.7 mg sodium chloride/ml |

Example 3

Case Report of Off-Label Treatment of NMO Patient with Cladribine

A woman of 32 years presented with acute visual symptoms and optic neuritis with normal head MRI. Episodic visual symptoms recurred with increasing severity up to complete blindness in one eye and episodes of deterioration in the other. Some response to methylprednisolone was noted. The diagnostic test for NMO-IgG (ELISA) was positive and brain MRI had no focal lesions.

20 mg of cladribine were administered subcutaneously to the patient on each of five dosing days, with one month or more separating the dosing days. On a dosing day, two vials were used each containing 10 ml of a solution of cladribine as shown in Example 2. Eight subcutaneous sites were used, each receiving an injection of 2.5 ml.

At the end of nine months blindness was complete bilaterally but motor and sensory functions were normal. The patient continued without further immunosuppressant treatment for two years without noted deterioration. After 2 years the patient was admitted with motor, sensory and autonomic symptoms. Based on new symptoms, abnormalities on spinal cord MRI and the previous NMO-IgG test the diagnosis was confirmed as neuromyelitis optica. After 3 months there was partial improvement but remaining mild paraparesis. Treatment with mitoxantrone was initiated but progressive deterioration (impaired walking, neurogenic bladder, blindness) led to the patient moving to another city for family support and she was lost to follow-up.

The progress of the woman diagnosed with NMO and treated with a total of 100 mg of cladribine is shown schematically in FIG. 1.

Note that the 100 mg received in total by the NMO patient is equivalent to a cumulative oral dose of approximately 250 mg when adjusted for oral availability.

Prior to cladribine treatment this patient experienced five episodes of worsening over four years (estimated annual relapse rate of 1.46). The intervening remission periods were 13, 15, 6 and 6 months. From initiation of an 8-month course of cladribine treatment she experienced 34 months of stable condition without reported relapses, followed by subsequent deterioration and other treatments. No adverse events attributed to cladribine were reported.

The individual affected appears representative of many newly diagnosed NMO patients. In particular, female sex and age of the patient are both typical of NMO (>80% female, and median age of onset in the fourth decade).

Further the absence of family history is consistent with the paucity of known genetic predisposing influences. Her relapses were treated with steroids, as is typically the case.

Thus in this case, a single course of cladribine treatment (100 mg s.c.) of NMO was associated with stabilization of the disease course for over two years. It is believed from this data that cladribine may be more effective in terms of period of remission compared to steroid treatment.

Example 4

In Vitro Treatment of Lymphocytes Derived from NMO Patients with Cladribine

Using the methods described in Laugel B. et al., *J. Neuroimmunol.*; (2011); 240-241; 52-57 peripheral blood mononuclear cells (PBMCs) are first isolated from blood obtained from healthy donors and NMO patients, for example by ficoll gradient centrifugation. T-lymphocytes are further purified from these PBMCs, by for example magnetic bead separation using a pan-T cell reagents, or CD4 reagents. The purified lymphocytes are maintained in culture using standard methods and reagents, for example RPMI-1640 growth medium.

To determine the cells' viability response to cladribine, identical numbers of lymphocytes purified from both healthy donor and NMO patients are cultured with one of a number of cladribine concentrations, ranging from for example one nanomolar to one hundred micromolar ($1 \times 10^{-9}$M to $1 \times 10^{-4}$M), or without any cladribine. After a period of several days, for example four days, the fraction of live cells is determined, for example by annexin V staining or trypan blue staining. This experiment is done either under stimulated conditions (that is, with the addition of anti-CD3 and anti-CD28 antibodies in all cultures, as below) or without these stimulating antibodies. Lymphocytes from NMO patients die over several days in a manner and to an extent similar to those purified from healthy donors, at similar concentrations of cladribine.

To determine the effect of cladribine on stimulated cytokine secretion by T lymphocytes from NMO patients, identical numbers of purified lymphocytes purified from both healthy donor and NMO patients are pre-incubated for less than one hour in medium containing one of a number of cladribine concentrations, ranging from for example one nanomolar to one hundred micromolar ($1 \times 10^{-9}$M to $1 \times 10^{-4}$M), or without added cladribine. Cells are then transferred, with their cladribine-containing or control medium, to the wells of culture plates coated with anti-CD3 antibody, and soluble anti-CD28 antibody is added. Secreted cytokines in culture supernatants collected after, for example, 24 hours, are determined by one of several standard methods including bead-based cytometric cytokine assay and enzyme-linked immunosorbent assay. Cytokines studied may include for example interferon-gamma, tumour necrosis factor, or interleukin-2. Secretion of cytokines by lymphocytes from NMO patients is inhibited by cladribine in a manner and to a degree similar to the inhibition seen in lymphocytes from healthy donors.

Discussion

This demonstrates that T lymphocytes from NMO patients respond to cladribine exposure with changes in their survival properties and functions that are expected to lead to beneficial effects on their disease, and that the unique disease condition of NMO has not induced changes in lymphocyte function that result in non-responsiveness, or inappropriate responsiveness, to cladribine exposure.

The invention claimed is:

1. A method of treating or ameliorating neuromyelitis optica (NMO) in a patient diagnosed with NMO and known to have (a) optic neuritis, (b) myelitis and (c) at least two of (i) MRI evidence of continuous spinal cord lesion 3 or more segments in length, (ii) onset brain MRI non-diagnostic for multiple sclerosis or (iii) NMO-IgG seropositivity comprising administering to the patient a pharmaceutical composition containing an effective amount of 2-chloro-2'-deoxyadenosine, hereinafter referred to as cladribine, or a pharmaceutically acceptable salt thereof and one or more pharmaceutically acceptable excipients.

2. The method according to claim 1 wherein the composition is presented in unit dose form.

3. The method according to claim 2 wherein the unit dose form is a tablet, a capsule or liquid formulation.

4. The method according to claim 1 wherein the effective amount of cladribine is administered orally.

5. The method according to claim 1 wherein the composition is administered daily as a single dose.

6. The method according to claim 1, wherein the effective amount is determined empirically as the cumulative amount of cladribine administered on between 5 and 20 dosing days, said 5 to 20 dosing days distributed over between 1 and 16 weeks, that results in a reduction in CD3+ T cells of between 30 and 80%, relative to pre-treatment levels.

7. A method of treating or ameliorating neuromyelitis optica (NMO) in a patient diagnosed with NMO and known to have (a) optic neuritis, (b) myelitis and (c) at least two of (i) MRI evidence of continuous spinal cord lesion 3 or more segments in length, (ii) onset brain MRI non-diagnostic for multiple sclerosis or (iii) NMQ-IG seropositivity comprising administering to the patient a pharmaceutical composition containing an effective amount of 2-chloro-2'-deoxyadenosine, hereinafter referred to as cladribine, or a pharmaceutically acceptable salt thereof and one or more pharmaceutically acceptable excipients, wherein the patient is treated with an effective amount of cladribine which is an effective cumulative amount over one or two years of from 1 mg/kg to 6 mg/kg.

8. The method according to claim 7 wherein the effective cumulative amount of cladribine over one or two years comprises from 1.5 mg/kg to 3.5 mg/kg.

9. A method of ameliorating neuromyelitis optica (NMO) symptoms in a patient diagnosed with NMO comprising administering to the patient a pharmaceutical composition consisting of an effective amount of 2-chloro-2'-deoxyadenosine, hereinafter referred to as cladribine, or a pharmaceutically acceptable salt thereof and one or more pharmaceutically acceptable excipients.

* * * * *